United States Patent [19]

Clevinger et al.

[11] Patent Number: 4,585,741

[45] Date of Patent: Apr. 29, 1986

[54] METHOD OF ASSAY FOR VITAMIN D METABOLITES

[76] Inventors: Brian L. Clevinger, 40 N. Kingshighway, St. Louis, Mo. 63108; John G. Haddad, 202 St. Georges Rd., Ardmore, Pa. 19003; Steven L. Teitelbaum, 536 Overhill Dr., St. Louis, Mo. 63130

[21] Appl. No.: 526,242

[22] Filed: Aug. 25, 1983

[51] Int. Cl.⁴ .................. G01N 33/536; G01N 33/82; G01N 33/53; G01N 33/531

[52] U.S. Cl. .................................. 436/542; 436/548; 436/804; 436/817; 436/825; 935/106; 935/108; 935/110; 435/68

[58] Field of Search ................................ 436/536–540, 436/548, 804, 817, 825; 935/106, 108, 110; 435/68

[56] References Cited

U.S. PATENT DOCUMENTS 4,119,647 10/1978 Liebman et al. .................. 260/397.2
4,269,777 5/1981 De Luca et al. .................. 260/397.1

OTHER PUBLICATIONS

Perry, III et al., Biochem. Biophys. Res. Comm. 112 (2), Apr. 29, 1983, 431–436.
Gray et al., Clin. Chem. 27(3) 458–463 (1981).
Dokoh et al., Anal. Biochem. 116, 211–222 (1981).
Eisman et al., Arch. Biochem. Biophys. 176, 235–243 (1976).
Gray et al., J. Clin. Endocrin. Metab. 299–306 (1977).
Perry et al., Internat. Workshop Vit. D., Williamsburg, Va., Feb. 1982, Abstracts, p. 70.

Primary Examiner—Christine M. Nucker
Attorney, Agent, or Firm—Scott J. Meyer; James W. Williams, Jr.

[57] ABSTRACT

The vitamin D metabolite, calcitriol, is determined in blood serum by radioimmunoassay employing monoclonal antibodies in which calcitroic acid serves as the immunogen.

4 Claims, 5 Drawing Figures

METHOD OF ASSAY FOR VITAMIN D METABOLITES

BACKGROUND OF THE INVENTION

This invention relates to a novel method of determining vitamin D metabolites.

It is well known that vitamin D plays an active role in the homeostatic mechanisms that control calcium metabolism. That is, this vitamin is involved in the precise control of the concentration of the calcium ion in plasma. Vitamin D is transported to various sites in the body where it is activated. The activated forms of the vitamin act on the target tissues, thereby causing an increase in calcium content. The activation of vitamin D is regulated in a negative feedback system by plasma calcium.

The most biologically active form of vitamin D is 1,25-dihydroxycholecalciferol or calcitriol, 1,25-$(OH)_2D_3$, which is formed by two successive hydroxylations of vitamin $D_3$. That is, calcitriol is formed by the sequential hydroxylation of vitamin $D_3$ at C-25 in the liver and at C-1 in the kidney. Various other analogs can be produced by hydroxylation at C-24 and C-26. Vitamin $D_3$, cholecalciferol, is produced in the body when the skin which contains the provitamin 7-dehydrocholesterol is exposed to sunlight.

Calcitriol functions primarily in intestinal calcium transport and bone calcium resorption. Abnormalities in the metabolism of calcitriol, as manifested by circulating levels of the compound, have been shown to play roles in the pathogenesis of a variety of diseases such as renal osteodystrophy, sarcoidosis and post-menopausal osteoporosis, a disorder which is endemic in western society.

Accordingly, the determination of circulating levels of calcitriol is of significant interest in the medical field. The assay of calcitriol in human blood serves as an excellent index of the status of vitamin D metabolism and provides a useful adjunct to other methods of determining vitamin D deficiency states.

Development of assay methods for calcitriol have been difficult because of its extremely low concentration in blood. Background information on these difficulties can be had by reference, for example, to Haussler et al., *New England J. of Med.* 297(19), 1041-50 (1977).

The principal assay for calcitriol in serum which has been developed heretofore is a radioreceptor assay, or competitive protein binding assay. This assay employs an ardously obtained, unstable rachitic chick intestinal binding protein. Moreover, due to the relative lack of specificity of this cytosolic receptor, each sample requires extensive chromatographic extraction and purification before it can be assayed. This standard assay which employs high pressure liquid chromatography (HPLC) is illustrated, for example, by Dokoh et al., *Anal. Biochem.* 116, 211-222 (1981);
Eisman et al., *Arch. Biochem. Biophys.* 176, 235-243 (1976); and
Gray et al., *J. Clin. Endocrin. and Metab.* 45, 299-306 (1977).

Because of these difficulties, the standard radioreceptor assay is performed only in a relatively few clinical laboratories. In an effort to procure more stable and specific reagents, polyclonal antibodies to vitamin D metabolites have been produced and used as high affinity binding agents in radioimmunoassays for these compounds. See, for example, Clemens et al., *Clin. Endocrinol.* 11, 225 (1979). Monoclonal antibodies share the stability of polyclonal antibodies, but can be readily screened for a particular specificity that will discriminate among a large number of closely related compounds as reported by Coffins et al., *J. Cell Physiol.* 79, 429 (1972). Since such clones could be theoretically maintained indefinitely, their development could circumvent present difficulties of the standard calcitriol serum assay. Previously, we have reported on a radioreceptor assay for calcitriol which employs a highly sensitive monoclonal antibody for the binding protein. Perry et al., *International Workshop on Vitamin D*, Williamsburg, Va., February 1982, *Abstracts*, p. 70. However, such assay still requires the use of high pressure liquid chromatography as an essential part of the assay. Said assay employs calcitriol bound to the carrier protein bovine serum albumin as the immunogen for preparing the monoclonal antibody.

BRIEF DESCRIPTION OF THE INVENTION

In accordance with the present invention, a novel radioreceptor method of determining vitamin D metabolites using monoclonal antibodies is provided in which the conventional high pressure liquid chromatographic extraction and purification step can be eliminated. Instead of using the conventional calcitriol coupled to carrier proteins as the immunogen for producing the monoclonal antibodies used in the radioimmunoassay, the novel method of the invention employs a different vitamin $D_3$ analog, namely, calcitroic acid or $1\alpha, 3\beta$-dihydroxy-9,10 seco-24-nor 5,7,10(19) cholatriene-23-oic acid.

DETAILED DESCRIPTION OF THE INVENTION

While the specification concludes with claims particularly pointing out and distinctively claiming the subject matter regarded as forming the present invention, it is believed that the invention will be better understood from the following description taken in connection with the accompanying drawings in which:

Figure 4:
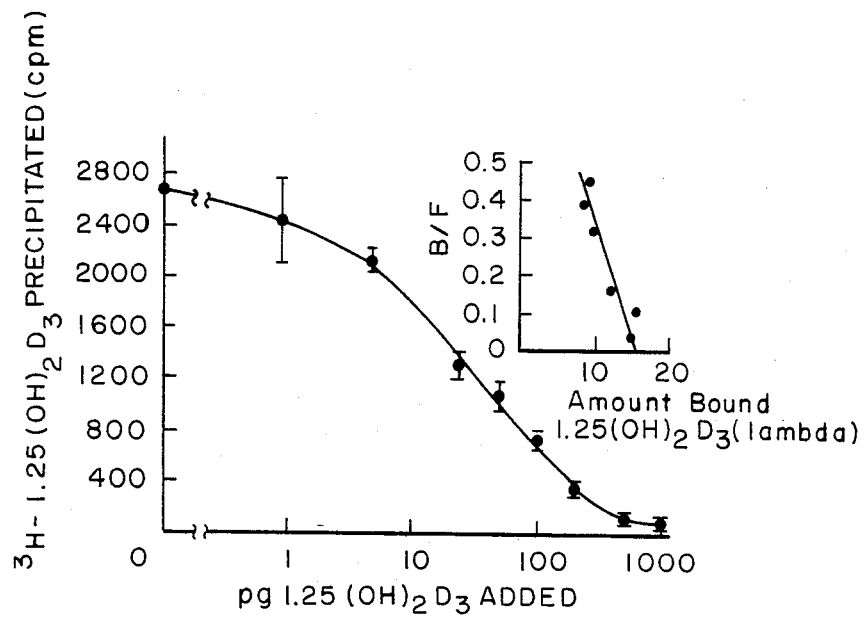

FIG. 4 shows the displacement curve for B2B4 monoclonal antibody (1:80,000 dilution) with radioligand and varying amounts of unlabeled 1,25-$(OH)_2D_3$. Counts bound equal the mean of three replicates containing antibody, radioligand and various amounts of 1,25-$(OH)_2D_3$ minus the mean of three samples containing only radioligand (no antibody present). The bars show the standard deviation for each point. The inset in FIG. 4 shows the Scatchard analysis of data presented (in which B is bound antigen and F is free antigen); apparent $K_D$ (equilibrium constant) is $3.3 \times 10^{-11} ML^{-1}$. ($ML^{-1}$=moles/liter) The Scatchard plot method is a common method for graphical analysis of ligand-receptor binding studies. Scatchard, *Ann. N.Y. Acad. Sci.* 51, 660 (1949). (One lambda=0.001 cc.)

Figure 5:
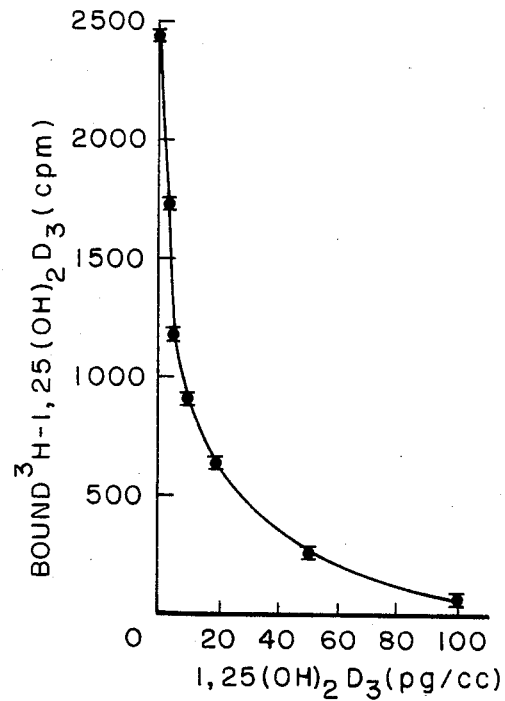

FIG. 5 shows the displacement curve for a preferred embodiment of a monoclonal antibody (B3A1) using $^3H$-1,25-$(OH)_2D_3$ and unlabeled 1,25-$(OH)_2D_3$.

In a preferred representative embodiment of the invention, the sample of human blood serum to be assayed is ether-extracted and chromatographed on a dextran gel column such as for example, Sephadex ® LH-20. This is a commercially available bead formed, cross-linked, dextran gel possessing both hydrophilic and lipophilic properties which is useful for separating lipophilic substances. It has an exclusion limit of about 4000 molecular weight. The appropriate fraction is incubated with both $^3H$-calcitriol and a monoclonal antibody which has been raised in mice, against bovine serum albumin-derivatized calcitroic acid. Bound tracer is separated from free by second antibody precipitation. A preferred antibody (B3A1) reversibly binds about 40% of $^3H$-calcitriol (8 pg/ml or ca. 8000 cpm). About half of these counts are displaced by about 7-8 pg/ml of unlabeled calcitriol. Thus, the assay detects levels of calcitriol at least as low as 2 pg/ml. The calculated $K_D$ of the preferred B3A1 antibody binding to the metabolite is $3.2 \times 10^{-12} ML^{-1}$, about 4½ orders of magnitude less than another analog of vitamin D, 24,25-$(OH)_2D_3$, and more than 6 orders of magnitude less than that of calcifediol or 25-OH $D_3$. Moreover, the antibody does not recognize 24,25-dihydroxycholecalciferol or 24,25-$(OH)_2D_3$ at concentrations as great as 100 ng/ml.

This degree of sensitivity and specificity has permitted establishment of a radioimmunoassay for calcitriol which does not require high pressure liquid chromatography. The radioimmunoassay in this preferred embodiment generates normal human serum values of 33.6±5.6 S.D. pg/ml which is within the reported normal range. (See Example 2, hereinbelow.) The recovery (about 90%) and sensitivity of the assay are such that only about one ml of serum is required for duplicate determinations. The accuracy and sensitivity of the assay method, using such relatively small volumes of blood, permit determination of calcitriol levels in groups of patients in whom this was not previously practical, such as small children.

The monoclonal antibody production can be carried out by conventional procedure such as described, for example, by Kohler and Milstein, *Nature* 256, 495-497 (1975); *Eur. J. Immunol.* 6, 511-519 (1976). According to this method, tissue-culture adapted mouse myeloma cells are fused to spleen cells from immunized mice to obtain the hybrid cells that produce large amounts of a single antibody molecule. In this procedure, calcitroic acid bound to the carrier protein, preferably bovine serum albumin, is used as the immunogen. The carrier protein, which can be natural protein molecules, synthetic peptides, or equivalent polymeric particles, is used to enhance immunogenicity of the calcitroic antigen. The albumins (e.g., human, bovine, or rabbit), synthetic peptides (e.g., polylysine) and polymers (e.g., polyvinylpyrrolidone) are commonly used as carriers for antibody production. The bovine serum albumin-derivatized calcitroic acid can be prepared by conventional general procedure such as described, for example, by Lieberman et al., *Rec. Prog. Hor. Res.* 15, 165 (1959).

A preferred mouse myeloma cell line for use in making these antibodies is the Sp2/0-Ag 14 cell line. This is a well-known cell line of BALB/c origin defined by Schulman, Wilde and Kohler, *Nature* 276, 269-270 (1978), the disclosure of which is incorporated herein by reference. These cells, which do not synthesize Ig chains, were obtained from the Basel Institute for Immunology and are available to the public from the American Type Culture Collection, Rockville, Md., under accession number ATCC CRL-1581. A preferred method of carrying out the fusion of the myeloma cells and the spleen cells is by the conventional general procedure described by Galfre et al., *Nature* 266, 550-552 (1977). This method employs polyethylene glycol (PEG) as the fusing agent for the cells growing as monolayers.

It will be appreciated that not all hybridomas prepared as described herein will have optimum antibody activity. As is customary in this field, radioimmunoassay procedures can be readily used to screen the population of hybridomas for individual clones which secrete the optimum specificity. The radioimmunoassay is based upon the competition between radiolabeled and unlabeled antigen (calcitriol) for a given amount of antibody which can be determined by conventional general procedure as described, for example, by Yalow et al., *J. Clin. Invest.* 39, 1157 (1960). Suitable methods using calcitriol as the antigen are described by Dokoh et al., *Anal. Biochem.* 116, 211-222 (1981); and Eisman et al., *Arch. Biochem. Biophys.* 176, 235-243 (1976).

The following detailed examples will further illustrate the invention although it will be understood that the invention is not limited to these specific examples.

EXAMPLE 1

Figure 1:
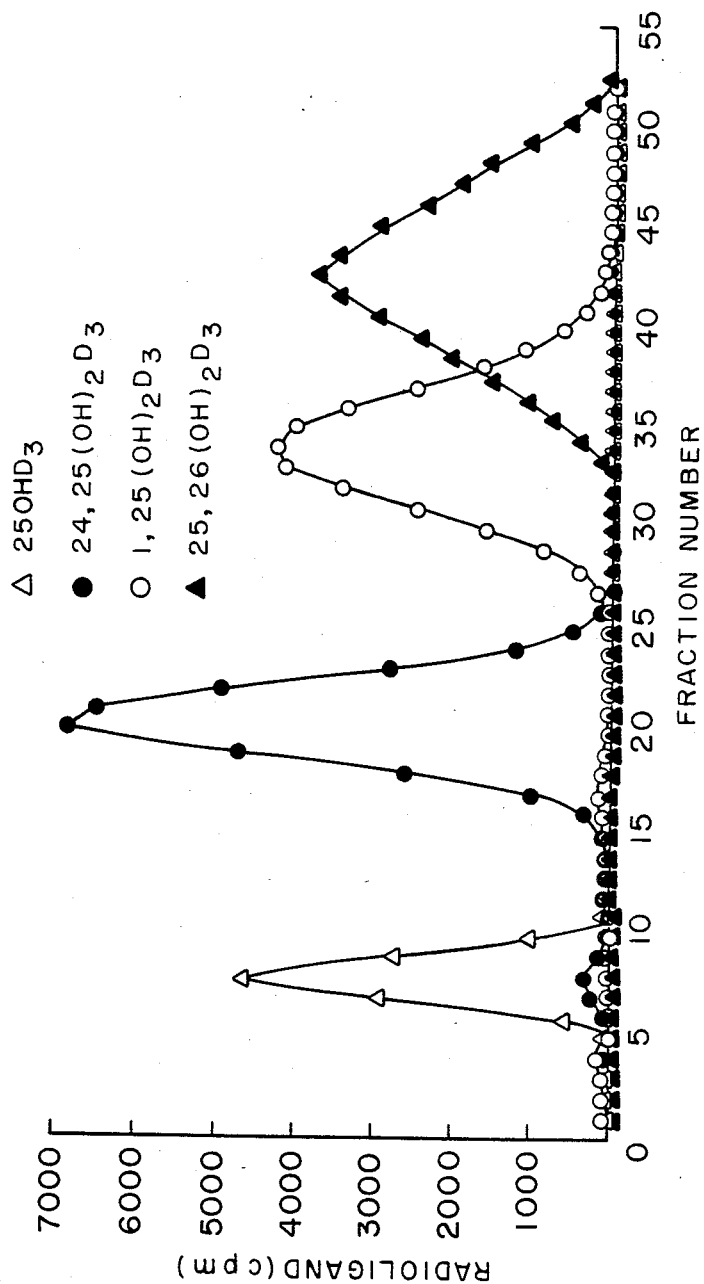
FIG. 1 shows the elution profile of the various vitamin D metabolites in an ether-extracted human blood serum sample chromatographed over a Sephadex ® LH-20 column.

Human blood serum samples are extracted in diethylether and dried under nitrogen. One ml of ether-hexane (35:65, v/v) is added to each dried sample and the solution chromatographed over a Sephadex LH-20 column. The elution profile of the various vitamin D metabolites placed on this column is shown in FIG. 1. Fractions 15 to 25, which contain calcitriol, 1,25-$(OH)_2D_3$, are collected (90% recovery). Small amounts of contaminating 25-OH $D_3$ (<1 ng) and 24,25-$(OH)_2D_3$ (<1 ng), and a relatively large proportion of total 25,26-$(OH)_2D_3$ (about 40% or 150 pg/ml) are also present in this peak. These pooled fractions are dried under nitrogen. 50 μl of ethanol is added to each sample and the radioimmunoassay is performed according to the following procedure. Unlike standard HPLC technique, these assays are run as a batch procedure permitting virtually unlimited number of simultaneous determinations.

Materials and Methods

All chemicals were purchased from Sigma Chemical Company (St. Louis, Mo.) unless otherwise noted. Calcitroic acid [1α, 3β-dihydroxy-9,10 seco-24-nor-5,7,10(19) cholatriene-23-oic acid] and unlabeled vitamin D metabolites were the unrestricted gift of Dr. Milan Uskokovic (Hoffmann-LaRoche, Nutley, N.J.).

Sterol conjugation—5 μmoles of isobutylchloroformate were added to calcitroic acid (5 μmoles) and triethylamine (5 μmoles), dissolved in 2 ml of cold, nitrogen-gassed dioxane (Baker, Phillipsburg, N.J.). After 20 minutes at 5°, this solution was stirred into 3.0 ml of water adjusted to pH 9:0 with 0.1N NaOH, containing 12 mg of bovine serum albumin (BSA) (Miles Laboratory, Fort Wayne, Ind.). The pH was maintained at 9.0 for 30 minutes. After magnetic stirring for six hours at 5°, the dioxane was evaporated under $N_2$ and the residual layer was extracted with equal volumes of diethyl ether (Mallinckrodt, St. Louis, Mo.) until the residues of two successive extracts exhibited no absorbance at 264 nm-when $N_2$ dried, and solubilized in 1 ml of ethanol. The aqueous layer was lyophilized, redissolved in 1 ml phosphate buffered saline, pH 7.4, and applied to a 1×17 cm column of G-25 Sephadex resin (Pharmacia, Piscataway, N.J.), equilibrated in the same buffer. The exclusion volume (Vo) was saved for spectral studies and protein assay by the method of Lowry et al. *J. Biol. Chem.* 193, 265 (1951). Ultraviolet spectroscopic studies of this preparation compared to those of BSA or calcitroic acid alone revealed an increase in absorbance at 264 nm consistent with the covalent conjugation of 5 moles of sterol per mole of protein. See Lieberman et al. *Rec. Prog. Hor. Res.* 15, 165 (1959). A similar synthesis was carried out using egg albumin.

Hybridoma production—BALB/c mice were immunized with 50 μg of calcitroic acid—BSA conjugate emulsified in complete Freund's adjuvant and boosted twice with antigen in saline at three week intervals. Four days after the final boost, spleen cells from these mice were fused with the Sp2/0-Ag 14 cell line described by Shulman et al. *Nature* 276, 269 (1978) using the method of Galfre, et al., *Nature* 266, 550 (1977). Cells were cultured in 24-well culture dishes in HAT (hypoxanthine, aminopterin and thymidine) selection medium described by J. W. Littlefield, *Science* 145, 709 (1964). Monoclonal antibodies binding calcitroic acid were detected in culture supernatants by a radioimmunoassay in which supernatants were exposed to microtiter plates coated with a calcitroic acid-egg albumin conjugate. Bound monoclonal antibody was detected with a $^{125}I$-labeled goat anti-mouse gamma globulin reagent. Cells from positive wells were cloned in soft agar over 3T3 cells as described by Coffins et al, *J. Cell Physiol.* 79, 429 (1972) and grown in BALB/c mice as ascites tumors.

Preparation of Monoclonal Antibody (B2B4)—Ammonium sulfate was added to ascitic fluid to 40% saturation. The mixture was incubated at 4° for one hour, centrifuged at 1000×g for 30 minutes, and the supernatant discarded. The pellet was dissolved in 0.025 M Tris-HCl buffer, pH 7.5 with 0.08 M NaCl (assay buffer) and fractionated on an AcA$_{44}$ column (1.5×45 cm) (LKB, Rockville, Md.) equilibrated in assay buffer. Antibody eluted in the void volume and Trasylol® trypsin inhibitor, 10 mM molybdate and 1 mM EDTA were added. This preparation was diluted 1:10 (initial ascitic fluid vol: final vol) and frozen in 1 cc aliquots at −20° C. until use.

Assays for 1,25-Dihydroxyvitamin $D_3$—1α,25-dihydroxy [26,27-methyl-$^3$H] cholecalciferol (specific activity 168 Ci/mmole) (Amersham/Searle, Arlington Heights, Ill.) was purified on a 1×40 cm column of Sephadex LH20 (Sigma) slurried in hexane: chloroform (65:35, v/v) and eluted in the same solvent as described by Gray et al, *J. Clin. Endocrin. and Metab* 45, 299 (1977). Antibody at appropriate dilution was incubated at 4° C. with reference 1,25-(OH)$_2$D$_3$ ranging from 1 pg-1 ng in 10λ of ethanol. In assays of binding specificity, 1,25-(OH)$_2$D$_3$, 24,25-dihydroxycholecalciferol [24,25-(OH)$_2$D$_3$] and 25-hydroxycholecalciferol (25- OHD$_3$) were used. 0.025 picomoles (10 μl) of radioligand were added; final assay volume was 1 cc. Radioligand was added after 1 hr pre-incubation in displacement assays; otherwise it was added immediately. After incubation for 18 hours, 10λ of rabbit anti-mouse Fab' (unrestricted gift of Dr. Judith Kapp-Pierce, Department of Pathology, Jewish Hospital of St. Louis and Washington University School of Medicine) was added with carrier mouse IgG and tubes were incubated for another 45 minutes at 4°. Alternatively, 20 λ of a partially purified preparation of carrier mouse IgG was added to the assay mixture. Then 40 λ of purified preparation of rabbit antimouse IgG was added and the mixture incubated for 4 hours at 4° C. Both gamma globulins were partially purified using DEAE—Affigel Blue (Biorad Laboratories, Richmond, Calif.). After centrifugation at 1000×g for 20 minutes, the supernatants were aspirated, the pellets suspended in Budget Solve (Research Products International, Mount Prospect, Ill.) and their radioactivity determined in a Beckman 7000 Scintillation Counter (Beckman Instruments Company, Palo Alto, Calif.).

For sucrose density gradient analysis, 350 λ of assay mixture or supernatant after immunoprecipitation was layered on a linear 5–20% sucrose gradient and centrifuged at 100,000×g for 17 hours. Molecular markers, human gamma globulin (16 mg/ml assay buffer) (Calbiochem-Behring, La Jolla, Calif.) and BSA (12 mg/ml assay buffer) were centrifuged identically. Fractions were collected through a bottom puncture apparatus and their radioactivity assayed.

RESULTS

Figure 2:
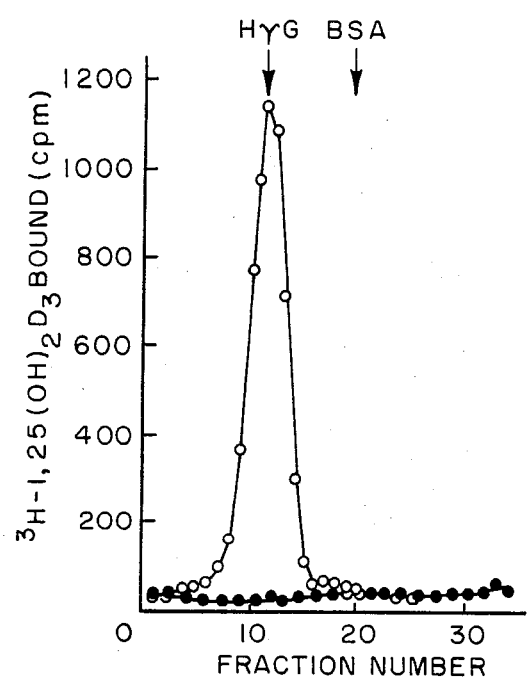
FIG. 2 shows linear sucrose density ultracentrifugation of one embodiment of a monoclonal antibody (B2B4) and $^3$H-1,25-$(OH)_2D_3$ before (o-o) and after (●-●) immunoprecipitation with 40 μl of purified rabbit anti-mouse gamma globulin. Human gamma globulin (HγG) and bovine serum albumin (BSA) peaks (determined by absorption at 280 nm) are indicated by arrows.

As shown in FIG. 2, partially purified B2B4 binds labeled sterol and sediments on sucrose gradient identically with human IgG immunoglobulin (150,000 daltons). When 1 ng/ml of 1,25-(OH)$_2$D$_3$ is added to the mixture prior to centrifugation, the radioligand is almost completely displaced (data not shown). Following immunoprecipitation by the addition of rabbit anti-mouse Fab', the antibody peak is lost but all of the radioactivity is recovered in the immunoprecipitate. (FIG. 2).

Figure 3:
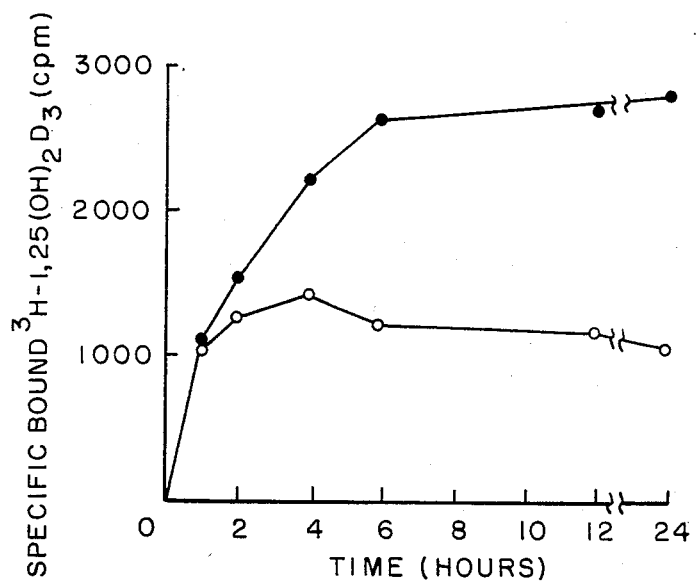
FIG. 3 shows the association of radioligand and B2B4 monoclonal antibody at 4° (●-●) and 22° (o-o). The specific counts bound equal the mean of three replicates containing antibody and radioligand minus the mean of three replicates containing antibody, radioligand and one ng of 1,25-$(OH)_2D_3$ at the indicated time point.

Using immunoprecipitation, the association kinetics of antibody and radioligand were then examined. Antibody B2B4 (1:80,000 dilution) and radioligand were incubated for various time intervals, immunoprecipitated and the radioligand in the pellet quantitated. As shown in FIG. 3, maximum binding is reached in 4 and 6 hours at 4° and 22°, respectively. The magnitude of specific binding is slightly higher at 4° C. Although the reasons for this observation are not readily apparent, this is a reproducible phenomena. Consequently, all further assays were performed at 4° C. for 18 hours.

FIG. 4 illustrates a displacement curve for this assay using a 1:80,000 dilution of partially purified B2B4. In the absence of unlabeled 1,25-(OH)$_2$D$_3$ approximately 3000 cpm are bound, half of the radioligand is displaced by 26 pg/ml of 1,25-(OH)$_2$D$_3$. Higher dilutions (1:120,000) of the B2B4 preparation can be used to reliably detect 1 pg/ml using this same displacement assay. The apparent $K_D$ at 1:80,000 dilution of the B2B4 preparation is $3.3 \times 10^{-11}$ML$^{-1}$. Thus, this preparation provides a high affinity binding protein for very sensitive serological assays. However, B2B4 does not discriminate well among various vitamin D$_3$ metabolites. At a dilution of 1:80,000 half of the reversibly bound $^3$H-

1,25-(OH)$_2$D$_3$ is displaced by 48 pg/ml 24,25-(OH)$_2$D$_3$ or 68 pg/ml of 25-OHD$_3$.

Calcitroic acid was used in the above example to produce an antibody directed against the A ring and 1α-hydroxyl moiety of 1,25-(OH)$_2$D$_3$. Since this conjugated compound lacks side chain carbons (C24-26), antibodies raised against this hapten might not recognize metabolites hydroxylated in those positions. Since this particular antibody (B2B4) displays only slight preference for the 1-hydroxyl metabolite, the specificity necessary to completely eliminate chromatography was not achieved in this example. However, the antibody is a superior assay receptor for 1,25-(OH)$_2$D$_3$ as compared to the rachitic chick intestinal binding protein. It has remained stable after repeated freezing and thawing and its binding characteristics are unchanged after fourteen months storage at $-20°$ C. At an antibody dilution of 1:120,000 the system can detect 1 pg/ml of 1,25-(OH)$_2$D$_3$, which is at least an order of magnitude less than normal circulating levels.

EXAMPLE 2

Example 1 is repeated except that another clone of the antibody (B3A1) is selected which has been found in the radioimmunoassay screen to have greater specificity for serum calcitriol than B2B4 of Example 1. B3A1 reversibly binds about 3300 cpm (40% of added $^3$H-1,25-(OH)$_2$D$_3$). FIG. 5 shows the displacement curve for this monoclonal antibody and demonstrates that the antibody recognizes levels of 1,25-(OH)$_2$D$_3$ as low as one pg/ml. The calculated K$_D$ for 1,25-(OH)$_2$D$_3$ is $3.2 \times 10^{-12}$ ML$^{-1}$. This specificity permits the complete elimination of the high pressure liquid chromatographic step.

The radioimmunoassay for calcitriol using monoclonal antibody of this example generates normal human serum values of 33.6±5 S.D. pg/ml which is within the reported normal range. The following Table I shows the levels of calcitriol in eleven normal individuals tested by the above method of the invention.

TABLE I

| Normal Patient No. | Calcitriol Level pg/cc |
|---|---|
| 1 | 33.5 |
| 2 | 38.4 |
| 3 | 36.9 |
| 4 | 38.2 |
| 5 | 19.7 |
| 6 | 34.6 |
| 7 | 34.5 |
| 8 | 34.2 |
| 9 | 30.2 |
| 10 | 29.9 |
| 11 | 39.5 |

For comparison purposes: Normal values (Bioscience Laboratories) = 20-76 pg/cc by standard HPLC assay.

Various other examples will be apparent to the person skilled in the art after reading the present disclosure without departing from the spirit and scope of the invention. All such further examples are included within the scope of the appended claims.

What is claimed is:

1. The method of determining the level of calcitriol in a blood serum sample comprising subjecting said blood serum sample to competitive protein binding radioimmunoassay by incubating with radiolabeled calcitriol and monoclonal antibodies, whereby said radiolabeled calcitriol competes physicochemically with nonlabeled calcitriol in said blood serum sample for binding sites on said monoclonal antibodies, and in which said monoclonal antibodies are produced by immunization with calcitroic acid as the immunogen.

2. The method of claim 1 in which the serum sample is ether-extracted and chromatographed on a dextran gel column to provide a concentrated calcitriol-containing fraction followed by incubation of said fraction with both radiolabeled calcitriol and a monoclonal antibody raised in mice against calcitroic acid as the immunogen coupled to carried protein, and thereafter separating bound tracer from the free and measuring the radioactivity.

3. The method of claim 2 in which the carrier protein is bovine serum albumin.

4. A monoclonal antibody useful in radioimmunoassay of vitamin D metabolites produced by fusion of mouse myeloma cells and spleen cells from a mouse immunized with calcitroic acid coupled to carrier protein.

* * * * *

UNITED STATES PATENT AND TRADEMARK OFFICE
CERTIFICATE OF CORRECTION

PATENT NO. : 4,585,741

DATED : April 29, 1986

INVENTOR(S) : BRIAN L. CLEVINGER, JOHN G. HADDAD and STEVEN L. TEITELBAUM

It is certified that error appears in the above-identified patent and that said Letters Patent is hereby corrected as shown below:

In Claim 2, col. 8, line 38, "carried" should be --carrier--.

Signed and Sealed this

Fifth Day of August 1986

[SEAL]

Attest:

DONALD J. QUIGG

Attesting Officer

Commissioner of Patents and Trademarks